United States Patent [19]
Neeley

[11] Patent Number: 5,368,477
[45] Date of Patent: Nov. 29, 1994

[54] COMPOSITE NEUROMUSCULAR ORAL DEVICE

[76] Inventor: Michael J. Neeley, 2039 Rose Hill, Carrollton, Tex. 75007

[21] Appl. No.: 103,422

[22] Filed: Aug. 6, 1993

[51] Int. Cl.$^5$ .............................................. A61D 3/00
[52] U.S. Cl. ........................................................ 433/6
[58] Field of Search .................. 433/6, 167, 169, 215, 433/229; 128/859, 861

[56] References Cited

U.S. PATENT DOCUMENTS

| | | | |
|---|---|---|---|
| 3,454,001 | 7/1969 | Stockfisch | 433/6 |
| 3,488,848 | 1/1970 | Lerman | 93/19 |
| 3,532,091 | 10/1970 | Lerman | 128/136 |
| 4,211,008 | 7/1980 | Lerman | 433/29 |
| 4,480,994 | 11/1984 | Hoffman | 433/6 |
| 4,559,013 | 12/1985 | Amstutz et al. | 433/6 |
| 4,727,867 | 3/1988 | Knoderer | 128/859 |
| 4,810,192 | 3/1989 | Williams | 433/6 |
| 5,194,003 | 3/1993 | Garay et al. | 433/215 |
| 5,203,701 | 4/1993 | Burtch | 433/6 |

*Primary Examiner*—Cary E. O'Connor
*Attorney, Agent, or Firm*—Reneé M. Larson

[57] ABSTRACT

According to the present invention, a removable base structure, which can be a partial denture framework of the type commonly used in the art, has a curved portion that fits along the inner surfaces of either the mandibular or the maxillary teeth, and two head portions that attach to one of the two ends of the curved portion and secure the base structure to either the mandibular or the maxillary teeth. A disposable cushion portion has two cushions that cover the occlusal surfaces of select mandibular or maxillary teeth and are secured to one of the two head portions by a male/female friction retention arrangement.

18 Claims, 1 Drawing Sheet

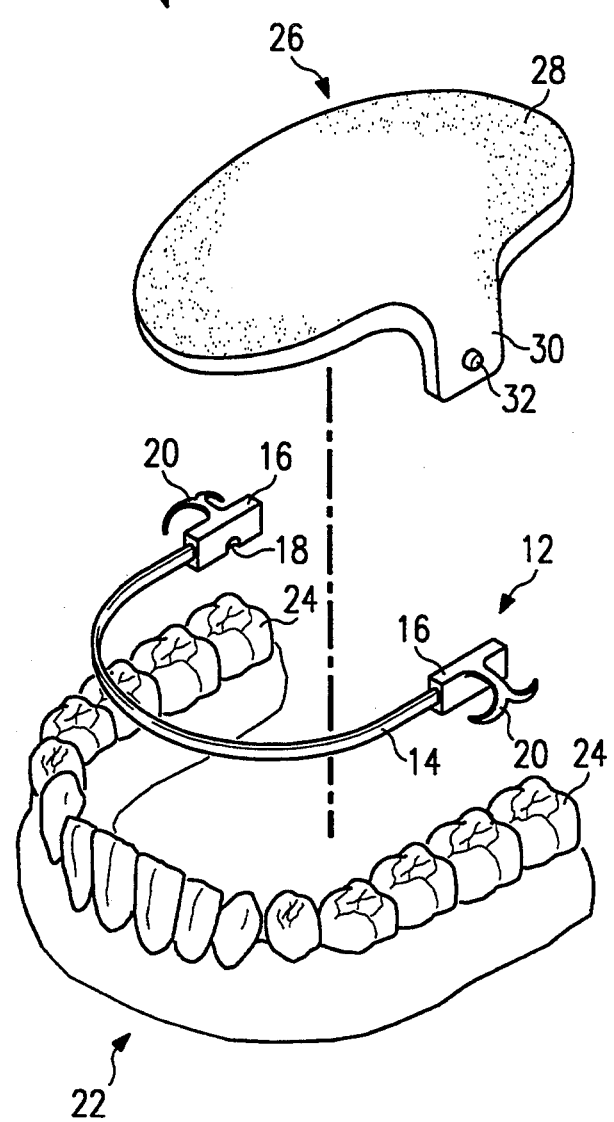

COMPOSITE NEUROMUSCULAR ORAL DEVICE

BACKGROUND OF THE INVENTION

1. Field of the Invention

The present invention relates to an auto repositioning neuromuscular oral device to be positioned in the human mouth for correcting various problems associated with occlusal pressure differences between the upper and lower jaw.

2. Description of the Prior Art

Patients who have differences in occlusal pressures between the upper and lower dental arches and between the left and right side of the mouth often suffer from painful masticatory muscle related disorders. Temporomandibular joint dysfunction (TMJ), as well as limited mandibular functioning, clicking or other noises in the jaw, and pain in the mouth, face, head, ears and neck are all common disorders that may be caused by a malocclusal condition.

Inter-occlusal disharmony can also be an etiologic factor associated with other seemingly unrelated neuromuscular disorders and can mimic such things as carpal tunnel syndrome, tennis elbow (fibrocitus), tendinitis of the elbow and shoulder, upper back pain, and other secondary symptoms of the head, face, neck, shoulders, and extremities such as the arms and hands. As the muscles of mastication become stressed through fatigue caused by differences in the inter-occlusal space between the left and right sides of the mouth, adjacent supporting muscles may brace or splint at their point of origin. This dysfunction may spread to the point of insertion of the muscles which, in turn, can trigger dysfunctional bracing or splinting of yet another adjacent muscle or muscle group (or fibers within the muscles) at the insertion point of the muscle group, causing a chain reaction. Because these disorders often exhibit no abnormality in the affected tissues and have no apparent proximity to the teeth, they have traditionally been viewed as being more medical than oral in nature. As a result, treatment has been directed at the symptoms and not the source, often with little success. On the other hand, patients having such secondary disorders who were treated for malocclusion, often obtained relief from these disorders.

In the treatment of temporomandibular joint dysfunction (TMJ) and other conditions caused by occlusion-muscle disharmony, the first phase of treatment is designed to obtain comfort and to restore proper functioning of the temporomandibular joint. At present, various types of acrylic splints may be used to obtain relief. A splint is a piece of hard acrylic that fits over either the top or the bottom teeth, covering occlusal surfaces of the teeth. It has the effect of taking pressure off the jaw joints, causing the jaws to be better aligned when biting down or otherwise closing the teeth. The purpose of these splints is to change the way the mandibular (bottom) and maxillary (top) teeth come together during normal activities such as swallowing, chewing and biting.

While splints are effective in correcting inter-occlusal problems, they do have limitations. Because splints are rigid, they must be periodically adjusted to accommodate the changes in the muscle tone and muscle length that always occur in the treatment of TMJ and other related disorders. Also, the hard acrylic material is inflexible in the mouth and may cause discomfort to the patient.

In addition to splints, another technique employed to treat these disorders is a device having a fluid filled cushion such as has been described in U.S. Pat. Nos. 3,488,848 and 4,211,008. Both these patents describe a repositioning fluid filled cushion. These patents are made of record hereto by the Information Disclosure Statement which accompanies this application.

U.S. Pat. No. 3,488,848 entitled "Intra-Oral Corrective Device" issued on Jan. 13, 1970 to M. D. Lerman. The device described therein has a fluid filled bite portion which provides for repositioning during the treatment of TMJ or other related disorders. However, the device floats unsecured in the mouth, therefore not providing the optimal amount of comfort and adjustment to the patient. Additionally, U.S. Pat. No. 3,488,848 does not provide for customization of the device to fit the size of the inter-occlusal opening of a particular patient's mouth, and, therefore, does not provide the most efficient and comfortable correction of the problem.

U.S. Pat. No. 4,211,008 entitled "Oral Device" issued on Jul. 8, 1980 to Lerman and discloses a fluid filled device which is positioned over the occlusal surfaces of the top teeth and has a labial portion which fits between the top lip and the front teeth. Such a device provides for repositioning of the inter-occlusal space, but floats freely in the mouth thereby causing less than the optimal amount of repositioning efficiency, stability, and comfort. Finally, the fluid-filled cushions described in U.S. Pat. Nos. 3,488,848 and 4,211,008 have been known to break or burst while in use.

Therefore, it would be desirable in the art to employ a composite neuromuscular oral device which is anchored while in the mouth so as to provide optimal repositioning integrity, stability, and comfort to the patient. It would further be desirable for the anchoring mechanism of such a device to utilize a structure well known and readily available in the art. It would additionally be desirable in the art for auto repositioning of the inter-occlusal space to be accommodated with various types of cushions.

SUMMARY OF THE INVENTION

Therefore, according to the present invention, an oral device provides for auto repositioning of the inter-occlusal distances to provide relief for TMJ and other related disorders.

A removable base structure has a curved portion that fits along the inner surfaces of either the mandibular or the maxillary teeth, and two head portions that attach to one of the two ends of the curved portion and secure the base structure to either the mandibular or the maxillary teeth. A disposable cushion portion has two cushions that cover the occlusal surfaces of select mandibular or maxillary teeth and are secured to one of the two head portions by a male/female friction retention arrangement.

BRIEF DESCRIPTION OF THE DRAWINGS

The novel features believed characteristic of the invention are set forth in the appended claims. The invention itself, however, as well as a preferred mode of use, and further objects and advantages thereof, will best be understood by reference to the following detailed description of an illustrative embodiment when read in conjunction with the accompanying drawing, wherein:

FIG. 1 is an expanded view of the oral device in a human mouth according to a preferred embodiment of the invention.

DESCRIPTION OF THE INVENTION

Referring to FIG. 1, an expanded view of oral device 10 in a human mouth is shown. Device 10 is comprised of two parts: base structure 12 and cushion structure 26.

Base structure 12 has a curved portion 14 which may be customized to precisely fit along the inner surfaces of bottom teeth 22, and a head portion 16 which has a slot 18 that is used to attach cushion structure 26 to base structure 12. Clasp 20 fits over the occlusal portion of molar tooth 24 and attaches to the outside surface of tooth 24 as shown, thereby ensuring that base structure 12 does not float. While base structure 12 is secured to an anchor tooth on the bottom teeth, in this case molar tooth 24, one skilled in the art will recognize that base structure 12 could as easily and effectively be secured to a patient's top teeth.

Base structure 12 is usually a removable partial denture framework of the type currently used in the dental arts and is normally composed of lightweight dental metal such as cast metal, gold, alloys, or other dental metals well known in the art. Acrylic denture resin could also be used to form base structure 12. Lightweight base structure 12 is more easily tolerated by the patient than the prior art hard acrylic splint.

Cushion structure 26 has cushion 28 which allows for auto repositioning of the jaw muscles as differences in the inter-occlusal spaces between the left and right sides of the mouth are adjusted and equalized. For simplicity, only one cushion structure 26 has been shown in FIG. 1; however, there would normally be two cushion structures 26, each one connected to one of the two head portions 16. Cushion 28 has a tab portion 30 which has a rigid tab 32.

Cushions 28 attach to base structure 12 by way of a male/female friction retention attachment (Tab 32, Slot 18). Use of a partial denture framework as base structure 12 allows for attachment of cushions 28 to the teeth, and holds them in place while the patient performs normal functions such as chewing and talking. Because base portion 12 is secured to the teeth by clasp 20 and cushion structure 26 is attached to base structure 12 by slot 18 and tab 32, several advantages may be realized. First, the oral device does not float, thereby contributing to efficiency in auto adjustment, comfort to the patient, and overall stability of the device. Second, the device offers distribution of inter-occlusal forces at a comfort level advantageous for patients, especially those suffering from headaches and oral facial pain. Additionally, the base structure 12 of the invention compensates for dental handicaps such as missing teeth; prior art devices do not compensate for such conditions.

While cushions 28 may be filled with fluids such as H$_2$O, saline solution, or a silicon derivative, this is not necessary so long as they offer the flexibility required to allow sufficient auto-repositioning of the patient's bite to occur. Additionally, non-fluid filled cushions provide the advantage of being less prone to rupture or breakage. For instance, cushions 28 may be made of silicon rubber or other materials which provide flexibility.

As described, cushions 28 attach to base structure 12 and rest on top of the occlusal surfaces of the posterior teeth. These cushions are removable and disposable, thereby allowing the patient to replace the cushions as they wear out and become non-functioning. The cushions allow for and adjust to the slightest change in the patients bite. The cushions are fit for the individual patient from the bicuspid to the molar position and accommodate differences in inter-occlusal space, and thus are offered in differing sizes such as small, medium, and large. The cushions may be accurately fitted during the laboratory phase of treatment.

Applicant's invention addresses the prior art problems described above. A two part structure provides for cushions to be secured to the occlusal surfaces of either the top or bottom teeth such that optimum auto repositioning of inter-occlusal distances may occur. The cushions are secured to the teeth by a male/female friction retention arrangement. An advantage of this method is that the need for periodic adjustments by the dentist is obviated. In addition to this, the repositioning dynamics of the appliance allow for continued automatic adjustments and subsequent relief. And, because cushion structure 26 is disposable, worn parts are easily replaced.

While the invention has been particularly shown and described with reference to a preferred embodiment, it will be understood by those skilled in the art that various changes in form and detail may be made therein without departing from the spirit and scope of the invention.

What is claimed is:

1. An oral device, comprising:
    a base structure having a curved portion with a first end and a second end, a first head portion connected to the first end of the curved portion and a second head portion connected to the second end of the curved portion, wherein the first head portion and the second head portion have a first clasp and a second clasp, respectively, for securing the base structure to either the mandibular or the maxillary teeth;
    a cushion structure having a first cushion with a first tab and a second cushion with a second tab; and
    a male/female friction retention structure for securing the cushion structure to the base structure.

2. The device of claim 1, wherein the friction retention structure comprises fitting the first tab into a first slot and the second tab into a second slot.

3. The device of claim 1, wherein the base structure is a removable partial denture framework.

4. The device of claim 1, wherein the first cushion and the second cushion cover the occlusal surfaces from the bicuspid to the molar teeth on both the right side and left side of the mouth, respectively.

5. The device of claim 4, wherein the first cushion and the second cushion are made of silicon.

6. The device of claim 4, wherein the first cushion and the second cushion are fluid filled.

7. The device of claim 6, wherein the first cushion and the second cushion are filled with water.

8. The device of claim 4, wherein the cushion structure is disposable.

9. An oral device, comprising:
    a partial denture framework having a curved portion which fits along the inner surfaces of the mandibular teeth with a first end and a second end, a first head portion having a first clasp and a first slot connected to the first end of the curved portion, and a second head portion having a second clasp and a second slot connected to the second end of the curved portion, wherein the first clasp and the second clasp secure the base structure to the mandibular teeth;

a cushion structure having a first cushion with a first rigid tab and a second cushion with a second rigid tab; and a male/female friction retention structure for securing the cushion structure to the partial denture framework.

10. The device of claim 9, wherein the friction retention structure comprises fitting the first rigid tab into the first slot and the second rigid tab into the second slot.

11. The device of claim 9, wherein the first clasp and the second clasp extend over the occlusal surface and attach to the outside surface of the right mandibular molar tooth and the left mandibular molar tooth, respectively.

12. The device of claim 9, wherein the first cushion and the second cushion cover the occlusal surfaces from the mandibular bicuspid tooth to the mandibular molar tooth on both the right side and left side of the mouth, respectively.

13. The device of claim 12, wherein the first cushion and the second cushion are made of silicon.

14. The device of claim 12, wherein the first cushion and the second cushion are fluid filled.

15. The device of claim 14, wherein the first cushion and the second cushion are filled with water.

16. The device of claim 12, wherein the cushion structure is disposable.

17. The device of claim 9, wherein the partial denture framework is made of lightweight dental metal.

18. The device of claim 17, wherein the partial denture framework is made of cast metal.

* * * * *